(12) United States Patent
Sarfati (10) Patent No.: US 7,258,660 B1
(45) Date of Patent: Aug. 21, 2007

(54) SPEECH THERAPY METHOD

(76) Inventor: Roy J. Sarfati, 19901 E. Country Club Dr., Suite 2 - 101, Aventura, FL (US) 33180

( * ) Notice: Subject to any disclaimer, the term of this patent is extended or adjusted under 35 U.S.C. 154(b) by 568 days.

(21) Appl. No.: 10/942,832

(22) Filed: Sep. 17, 2004

(51) Int. Cl.
*A61F 5/58* (2006.01)

(52) U.S. Cl. .................. 600/23; 600/300; 128/898; 704/270; 434/185; 434/353

(58) Field of Classification Search .............. 600/23, 600/300; 128/898; 704/270; 434/185, 353
See application file for complete search history.

(56) References Cited

U.S. PATENT DOCUMENTS

| | | | |
|---|---|---|---|
| 3,566,858 A | 3/1971 | Larson | |
| 4,012,852 A | 3/1977 | Journot et al. | |
| 4,020,567 A | 5/1977 | Webster | |
| 5,231,500 A | 7/1993 | Miyaji et al. | |
| 5,289,521 A | 2/1994 | Coleman et al. | |
| 5,647,834 A | 7/1997 | Ron | |
| 5,733,129 A | 3/1998 | Fayerman et al. | |
| 5,765,135 A | 6/1998 | Friedman et al. | |
| 5,791,904 A | 8/1998 | Russell et al. | |
| 6,231,500 B1 * | 5/2001 | Kehoe | 600/23 |
| RE37,684 E | 4/2002 | Shpiro | |
| 6,971,972 B1 * | 12/2005 | McGovern et al. | 482/3 |
| 7,031,922 B1 * | 4/2006 | Kalinowski et al. | 704/271 |

* cited by examiner

*Primary Examiner*—Thao X. Le
*Assistant Examiner*—Aaron B Colquitt
(74) *Attorney, Agent, or Firm*—Kenneth E. Merklen (57) ABSTRACT

An improved stuttering treatment program provides for a multi dimensional diagnostic procedure for identifying the problems associated with stuttering. A simultaneous attitude modification phase and a speech fluency enhancing techniques phase define a supervised, hands-on exercise portion of the program which is intended to advance the level of speech of a stutter afflicted person to speech fluency. Upon completion of attitude modification and speech fluency enhancing exercises, which raises the patient to speech fluency, a self-discipline phase of the program is provided where the patient supervises himself during speech exercising, monitors and analyzes exercise effect and reports his analysis to speech professionals. The self-supervised exercise is up-dated and communicated to the patient, for preventive maintenance of speech fluency.

16 Claims, 6 Drawing Sheets

POST TREATMENT MAINTENANCE MONITORING

SPEECH THERAPY METHOD

BACKGROUND OF THE INVENTION

1. Field of the Invention

The present invention relates to treatment or therapy of speech disorders. In particular, the present invention is a fully integrative therapy program for relief of the speech disorder of stuttering.

2. Prior Art

Stuttering is a communicative disorder which has a negative impact on a person's ability to make verbal communication with other person or persons, with physiological negative side effects impacted on the person affected with the stuttering condition. Side effects from the inability to make, what is considered, normal verbal communication, effect the afflicted person psychologically and physically. The mental condition of a person afflicted with stuttering is often expressed socially, in different negative impacts according to the then current environment. The afflicted person may have one negative social impact in a family environment, a different, negative social impact with friends, away from the family environment and a third, totally different negative social impact in an environment with strangers. Side effects of stuttering are not limited to the afflicted person but often have a negative effect on persons listening to a person who stutters.

Conditions that cause stuttering vary greatly. Some conditions may be physical, some may be psychological, with a combination of both conditions often occurring. The physical condition may be a physical deformation or the inability to use physical elements properly or negative habits. Negative habits usually are developed early in life and are usually difficult to overcome. The struggle for fluent speech communication is evident in both children and adults. Therapy that should be individual and personal is often individual but not personal.

Prior treatment programs to overcome stuttering have been limited by addressing the problem of stuttering only, or in conjunction with the emotional aspect of the individual afflicted with stuttering. The behavior aspect has been treated by correction and repetition while the emotional aspect has been treated through a psychoanalytical approach and/or medication, which often has its own negative side effects. The bending and changing of early developed habits is a difficult challenge and once the habit is overcome reversion to the old habit is easy for the person, when the pressure of corrective action is removed.

Treatment for overcoming the problem of stuttering may be found, in a limited approach, in the prior art. The U.S. Pat. No. 5,289,521 issued to Coleman et al in February 1994, teaches a computer network system for treating a plurality of verbally handicapped persons, remotely, during the same period of time. A local interface to a central computer system is provided so that a speech therapist and/or a verbally handicapped person can communicate with a central speech development computer. Speech exercise selection may be made remotely. This impersonal system addresses only a fraction of the problems attendant speech disorders and/or defects. The U.S. Pat. No. 4,020,567 issued to Webster in May 1977, teaches a method of speech therapy for persons who stutter. The method taught is limited to monitoring response adequacy and repetitive syllable formulation. This therapy is used to overcome the problem of stuttering. However, this teaching addresses only the physical and vocal problems attendant the speech disorder of stuttering. The U.S. Pat. No. 4,012,852 issued to Journot et al in March 1977, teaches the limited use of an electronic scoring apparatus which times, scores and displays both time and score to a person engaged in speech correction exercises. The U.S. Pat. No. 5,647,834 issued to Ron in July 1997, teaches a biofeedback speech correction system which is essentially a speech-training system. The voice of a speaker is monitored and, from the spoken words, the emotional state of the speaker is determined. A biofeedback system coupled to the speaker, alters one or more physiological variable characteristics of the emotional state of the speaker, generating speech correction. This teaching does not address correction of speech impairments, rather it alters the on-going state of mind of a speaker. U.S. Pat. No. 5,733,129 issued to Fayerman et al in March 1998, teaches the use of an electronic timer to provide timed commands for rhythmically inhaling, speaking and exhaling for developing positive speech habits. This teaching addresses the breathing and speaking aspects of correcting the speech pattern of a person who stutters while other, more basic problems attendant this speech disorder remain unaddressed by this teaching. U.S. Pat. No. 5,765,135 issued to Friedman et al in June 1998, teaches a speech therapy system which monitors voice data and breathing data of a person and converts the data from analog to digital form. Although this teaching may simplify the processing of data, the teaching fails to address problems attendant speech impairments. The U.S. Pat. No. 5,791,904 issued to Russell et al in August 1998, teaches a speech training aid for assisting a person in changing speech habits or speech influences such as territorial speech characteristics. This teaching addresses the problems of speech and/or word elegance. U.S. reissued patent #US Re37,684E issued to Shpiro et al in April 2002 on U.S. Pat. No. 5,487,671 issued January 1996, teaches apparatus for interactive speech training. Prerecorded specimens of speeches are played to a person for attempted imitation or mimicking for improving speaker techniques. A computer database has prerecorded speeches classified according to age, gender and/or dialect for selection by the user. A person who is afflicted with the speech disorder of stuttering is identified as 'stutterer'. Authority for this identification is the Random House Webster's College Dictionary, Copyright 1995, 1992, 1991.

SUMMARY OF THE INVENTION

The present invention provides an integrative therapy program for patients who stutter, which may be defined as a multi-dimensional, progressive process or method for actively overcoming speech problems of stuttering, for a person afflicted with the same, and for maintaining and managing fluent speech of that person, after hands-on therapeutic action has achieved speech fluency and the hands-on therapeutic action has ceased. In accordance with the invention, a person afflicted with the speech disorder of stuttering, or a stutterer, is examined to determine the extent and depth of the problem, the collateral problems and/or characteristics influencing the dominant problem and the environmental influences on both the person and the problems. From this multi-dimensional, in-depth diagnostic examination, an individual, personalized therapeutic program is generated, for relieving and/or correcting the speech disorder, tailored specifically to the person's or patient's requirements. Psychological and physiological parameters and characteristics are considered. Vocal parameters, respiratory pattern, facial muscle and laryngeal structure and function are analytically examined against established norms for the particular patient. These concomitant characteristics define the patient's problems that need be addressed. The present stuttering treatment program is employed, preferably by a competent team of medically trained personnel, such as, at least a speech therapist and a psychologist, for example, work together, at a Center, where the person who stutters is treated, to develop a multi-dimensional diagnosis from which a personal, active program for overcoming the dysfunctions of the patient, is derived. The derived program may include some options, which, where the patient is of a capacity to make decisions, are selected or made by the patient. If the patient is a child and/or a person without decision making capacity, selections, best for the patient, are made for him or her, or by a parent or guardian and/or attending personnel. An hands-on, progressive program is established, with periodic review of accomplishment by the patient, and upon achieving the results desired, the active hands-on phase of the program ceases. The hands-on progressive program may be defined as a series of vocal communication exercises. The communication exercises involve the use and practice of stimuli, phoneme and respiratory characteristics in a series of sessions of increasing complexity, with anticipated results. The hands-on progressive program is completed when the patient attains the anticipated results, which are speech fluency.

The hands-on, progressive training or exercise program may be defined as a series of vocal communication exercises that involve the use and practice of stimuli; phoneme; and respiratory characteristics, in a series of phases or stages of increasing complexity, with anticipated results. A preferred program of progressive exercises has a duration of three (3) five (5) day weeks, from start to completion or finish. A training or exercise day is preferably divided into five (5) 20 minute sessions with each session followed by a break for review, questions and discussion with the attendant team. A lunch break may define one of the review breaks and may be extended in time. A sixty (60) minute general review may follow the last training or exercise session of the day. The preferred schedule may be changed, if desired, according to the needs of the patient, however, it is preferred that a schedule of sessions be established and adhered to so that progress of the course of treatment maintains its intended continuum.

Upon completion of the hands-on progressive program, the patient enters a self-administered phase of the program, designed for maintaining the speech fluency achieved through the active, hands-on phase of the program. The self-administrated, self-disciplined phase, which has preventive maintenance effect, includes self-administered exercises with self-evaluation of speech fluency and exercise effectiveness with self-evaluation data reported to the Center. A review of the self-evaluation report and consultation with the released patient up-date the self-treatment to maintain the speech fluency achieved. Theoretically, patient status of a person having been accepted for treatment under the program, and having achieved speech fluency, after having been afflicted with stuttering, is continuous.

Psychological and physiological characteristics related to stuttering can be apparent at an early age and give rise to undesirable habits. These habits are difficult to overcome and/or correct as they become chronic and are reluctant to remain suppressed once they have been overcome and the corrective pressures have been reduced or removed. Self help, with assistance from professional persons, defines preventive maintenance which promotes continued fluent speech production.

OBJECTS OF THE INVENTION

It is an object of the invention to provide a multi-dimensional diagnostic method or process for formulating and carrying out an individualized, personal program for overcoming the speech disorder of stuttering. The diagnostic process evaluates patient attitude from psychological and physiological aspects, with the physiological aspects extended to structural characteristics, muscular characteristics and usage characteristics.

Another object of the invention is to address the physiological aspect of the emotional disorder associated with stuttering, using complimentary medicine techniques, invasive and non-invasive in nature, where medicine is tailored to the patient's needs and implementation is based on a viable schedule peculiar to the patient.

A further object of the invention is to address the physiological aspect of the speech disorder using non-invasive complimentary medicine. The treatment protocol is established based on the needs of the particular patient.

It is another object of the invention to provide an improved system for tracking patient performance during the treatment phase and the post-treatment phase of the stuttering correction program and/or method disclosed herein. Pre-treatment opinion and recommendations, with expected results, are stored in the central computer database and are displayed on a personal and/or medical need to know basis. Active treatment results are stored and displayed in a personal interactive manner on the patient's monitor, with display in real time. Post-treatment personal evaluation, monitoring and maintenance, with results pertaining to specific troublesome areas are reported to and stored in the central computer database for personal use of the patient and/or for profession evaluation.

A still further object is to provide an improved process for providing a corrective audio-visual feedback system in a therapeutic stuttering correction program. Correct response to active exercise is provided in a digitalized auditory manner. Corrective visual feedback is provided via user-friendly diagrams.

It is another object of the invention to provide a personal stuttering treatment or correction program that incorporates a fully integrated, multi-therapeutic program with professional team review of patient self-evaluation of the effectiveness of self-treatment during the post-treatment, preventive maintenance phase of the stuttering correction program.

A further object of the invention is to provide a personalized stuttering treatment program characterized by an hands-on active treatment phase and a post active treatment, self-disciplined phase which includes self-administered activity, self-evaluation, report to center of self-evaluation, review of self-evaluation by professional personal and updating of self-administered activity for preventive maintenance against patient fluency regression.

DETAILED DESCRIPTION OF THE INVENTION

Figure 1:
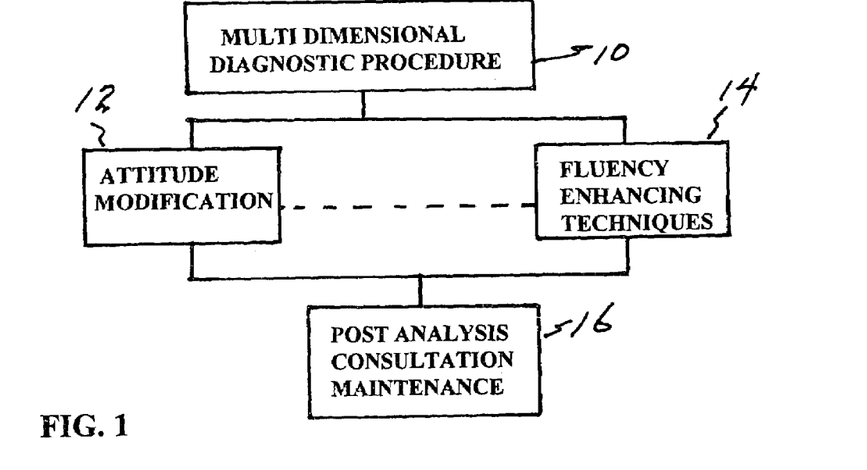
FIG. 1 is a flow chart representing the phases of the integrated stutter treatment program.

The flow chart presented in FIG. 1 represents the general steps or phases of the integrated stuttering treatment protocol. Each step represented in the flow chart in FIG. 1 is more fully defined in the FIGS. 2, 3 and 4. Block 10, MULTI-DIMENSIONAL DIAGNOSTIC PROCEDURE, is more fully represented and/or defined by the flow chart in FIG. 2. Block 12, ATTITUDE MODIFICATION, is more fully represented and/or defined by the flow chart in FIG. 3. Block 14, FLUENCY ENHANCING TECHNIQUES, is more fully represented and/or defined by the flow chart in FIG. 4. Block 16, POST ANALYSIS/CONSULTATION/MAINTENANCE, is more fully represented and/or defined by the flow chart in FIG. 5. The broken line between blocks 12 and 14 represents that these functions are executed simultaneously.

Figure 2:
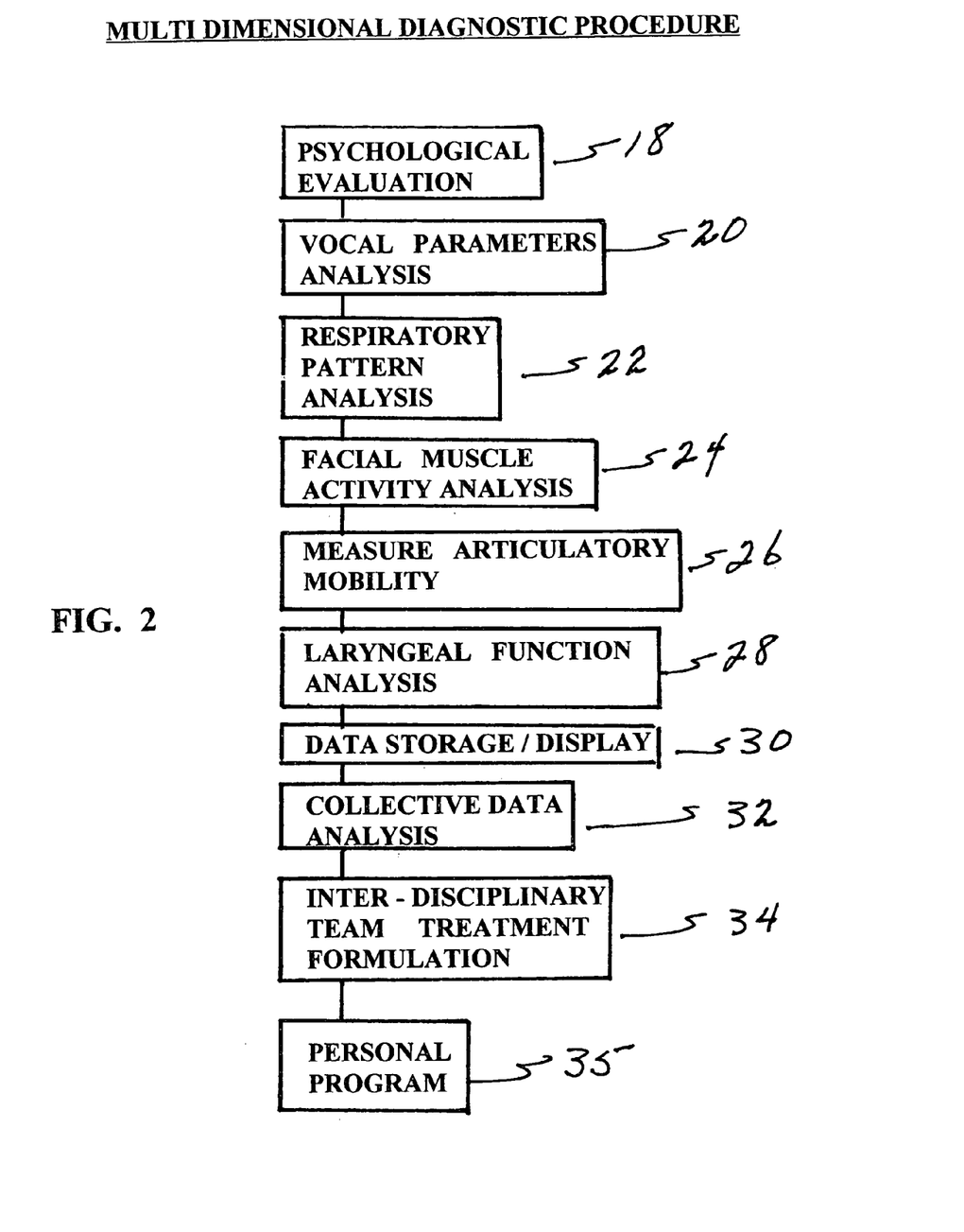
FIG. 2 is a flow chart representing, in more detail, the Multi Dimensional Diagnostic Procedure phase represented in FIG. 1.

As represented by the flow chart in FIG. 2, the MULTI-DIMENSIONAL DIAGNOSTIC PROCEDURE, block 10, is defined by a protocol where a patient initially goes through a comprehensive series of evaluation and analysis of factors that may have an effect on the stuttering problem of the patient. The objective of PSYCHOLOGICAL EVALUATION, block 18 is to define the feelings and attitude of the patient caused by or developed as a result of stuttering. The objective of the VOCAL PARAMETERS ANALYSIS, block 20, is to analyze and establish the vocal pitch, vocal intensity and vocal cycle of the patient, for determining the depth of the patient's fluency disorder. This may be accomplished with the assistance of a computer programmed to interrogate these parameters of the patient and record the results. The patient's respiratory pattern, block 22, RESPIRATORY PATTERN ANALYSIS, is analyzed and evaluated to determine functional problems that must be addressed with respect to the patient's use of his or her breathing capabilities. This may be accomplished by using a device that measures the efficiency of the use of the breath for phonation. FACIAL MUSCLE ACTIVITY ANALYSIS, block 24 provides data on the patient's use of facial muscles relative to phonation. Facial muscle activity may be analyzed using a non-invasive electrode instrumentation system where sensor contact is made on specific areas of the face which relate to phonation. MEASURE ARTICULATORY MOBILITY, block 26 may be accomplished using real time video processing, which may permit the examining person to view the patient's oral motor function during simple and complex motor speech acts. The function and use of the larynx is measured and analyzed, LARYNGEAL FUNCTION ANALYSIS, block 28. Larynx usage may be determined using an instrument which includes non-invasive electrode sensors which are placed at the thyroid region for detecting and measuring the Lx wave format, characterizing the impedance changes that occur during a vocal cord vibration cycle.

The results of the examinations are evaluated, defining the following clinical results;

Respiratory-communicative patterns;
Vocal pitch;
Vocal intensity;
Vocal cycle Periodicity/Aperiodicity pattern;
Lingual-Alveolar position and movement;
Lingual-Palatal position and movement;
Lingual-Velar position and movement
Localization of facial spasms; and
Degree of facial contractions.

The results of the several examinations and analyses are recorded and stored for study and displayed to the patient and the medical personnel who have responsibility for the patient, block 30, DATA STORAGE/DISPLAY and the collective data is analyzed, block 32, COLLECTIVE DATA ANALYSIS. The medical team of healthcare professional people, including at least a psychologist, a speech and/or language pathologist and a complementary medicine specialist, review and correlate the collected data and develop a treatment program, block 34, INTER-DISCIPLINARY TEAM TREATMENT FORMULATION, that is personal and specific, block 35, PERSONAL PROGRAM, for the interrogated patient.

Figure 3:
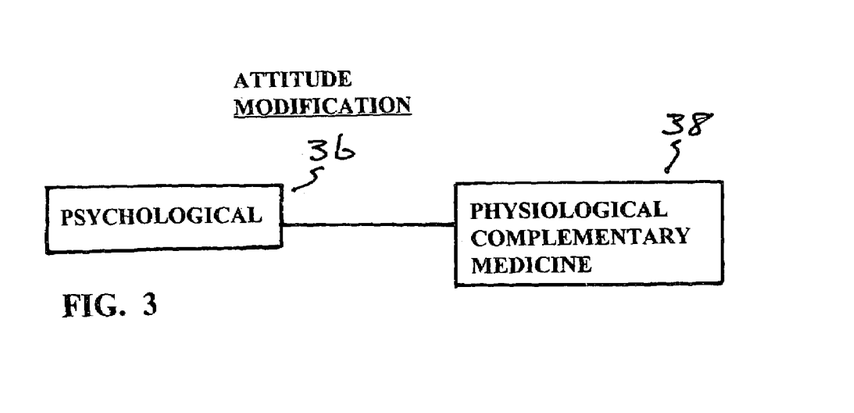
FIG. 3 is a flow chart representing, in more detail, the Attitude Modification phase represented in FIG. 1.

FIG. 3 represents and/or defines more fully, block 12, the Attitude Modification step of the integrated stuttering treatment program represented in the general flow chart, FIG. 1. The emotional attitude is addressed psychologically, block 36, PSYCHOLOGICAL, and the physical aspect is addressed with non-invasive medicine, block 38, PHYSIOLOGICAL COMPLEMENTARY MEDICINE. Complementary medicine may include Low Level Laser sessions, Acupuncture and Homeopathic formulations which address symptoms of, for example, anxiety, emotional communicative stress and tonic/clonic spasms. The stages of coping with emotional stress and anxiety associated with stuttering consist of:

Identification of the problem;
Acceptance of the problem; and
Management.

As the patient gains control over his or her emotional disorder, the patient simultaneously goes through a program of fluency enhancing techniques, specifically designed for the patient.

Figure 4:
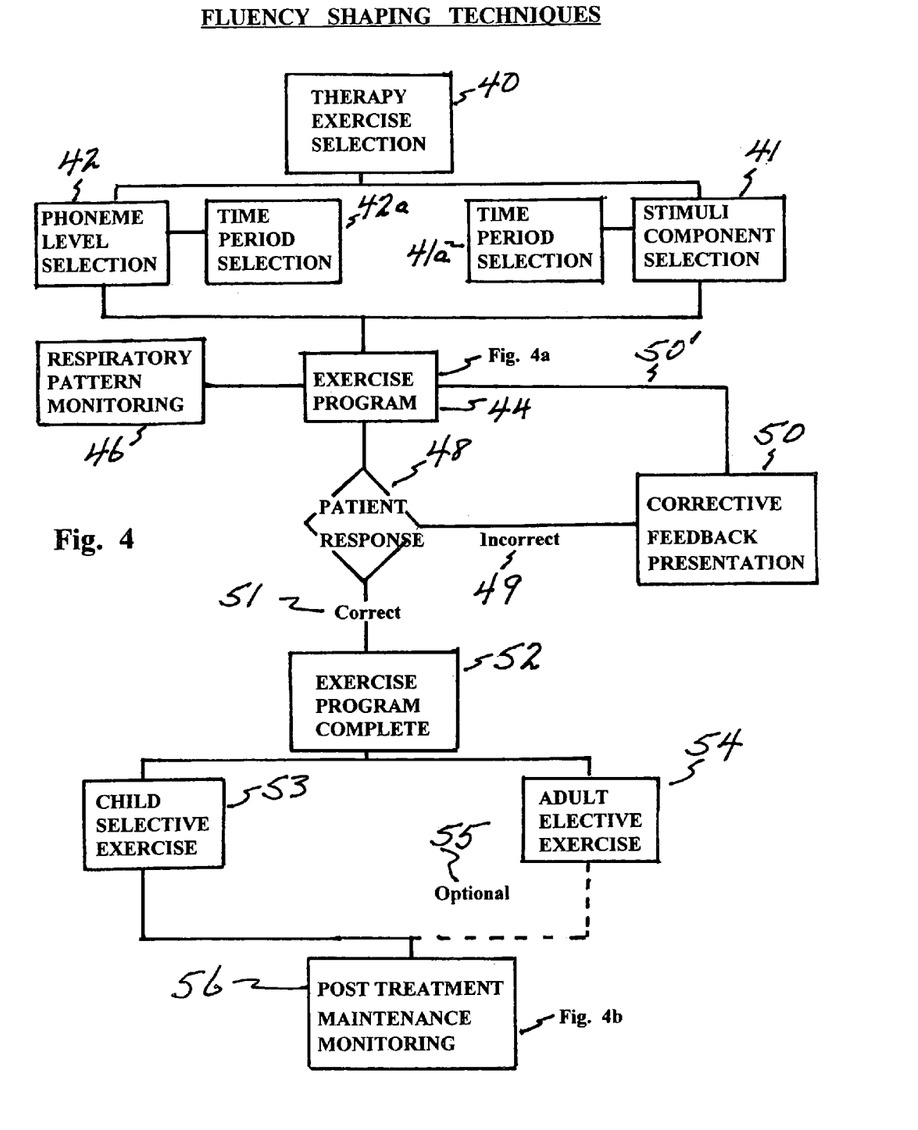
FIG. 4 is a flow chart representing, in more detail, the Fluency Enhancing Techniques phase, represented in FIG. 1.

FIG. 4 represents and/or defines a preferred embodiment of block 14, FLUENCY ENHANCING TECHNIQUES, represented generally in FIG. 1. The fluency enhancing techniques are visual, tactic and audio aids, designed to interact and complement each other, such as Syllable extension;
Gradual vocalization; and
Maximal respiratory enhancement.

These techniques are designed to teach the stuttering patient, or stutterer how to establish control over various motor speech acts; to teach the patient how to apply minimal pressure during motor speech acts and how to utilize breathing as the main source of energy for effective communication.

Stuttering therapy exercises, in each of two protocols, are selected, Block 40, THERAPY EXERCISE SELECTION, for the patient, based on the protocol defined in FIG. 2. One protocol of exercise is STIMULI, another protocol of exercise is PHONEME. Utilization of the respiration function, RESPIRATORY PATTERN MONITORING, block 46, is monitored and administratively adjusted during performance of these exercises. The STIMULI COMPONENT SELECTION, block 41, is preferably defined in a plurality of phases, Phase I is an exercise covering the repetition of Isolated Syllable Segments. The Phase I exercise covers speech sounds which are individual, in single syllable units. Phase II is an exercise covering the repetition of Integrated Syllable Segments. The Phase II exercise covers speech sounds in varying complexity syllable units. Phase III is an exercise covering the repetition of Sentence Construction Units. The Phase III exercise covers the vocalizing of sentences in systematic complexity containing the elements of Phases I and II. Phase IV is an exercise covering Interactive Dialogues during which the patient practices making statements with computer follow-up of the statements. A Stimuli Component, Phase V exercise may cover Interactive Dialogue with Programmed Disturbances. During Phase V of the exercise, the patient practices making statements in the face of interruptions during presentation of a statement, the interruptions occur randomly, in various duration and intensity. Stimuli exercises may also include additional phases, such as practicing conversations between and/or among persons on a particular topic; role-playing, as in acting, for example; giving directions; and, simulated interview, such as simulated job interview, for example.

The PHONEME LEVEL SELECTION, block 42, is preferably defined in four (4) levels, a Phoneme Level comprising speech sounds that are organized based on vocal tract constriction and vocal pressure initiation onset. The four phoneme levels are defined as Phoneme Level I, vowels; Phoneme Level II, sustained consonants; Phoneme Level III, partial vocal tract constriction consonants; and, Phoneme Level IV, complete vocal tract constriction consonants. The time elements, represents in blocks 41*a* and 42*a*, TIME PERIOD SELECTION, are defined by intervals of time of the exercise periods and the time intervals between exercise periods. These time intervals are selected by the patient where the patient is capable of meaningful selection of time.

Figure 4A:
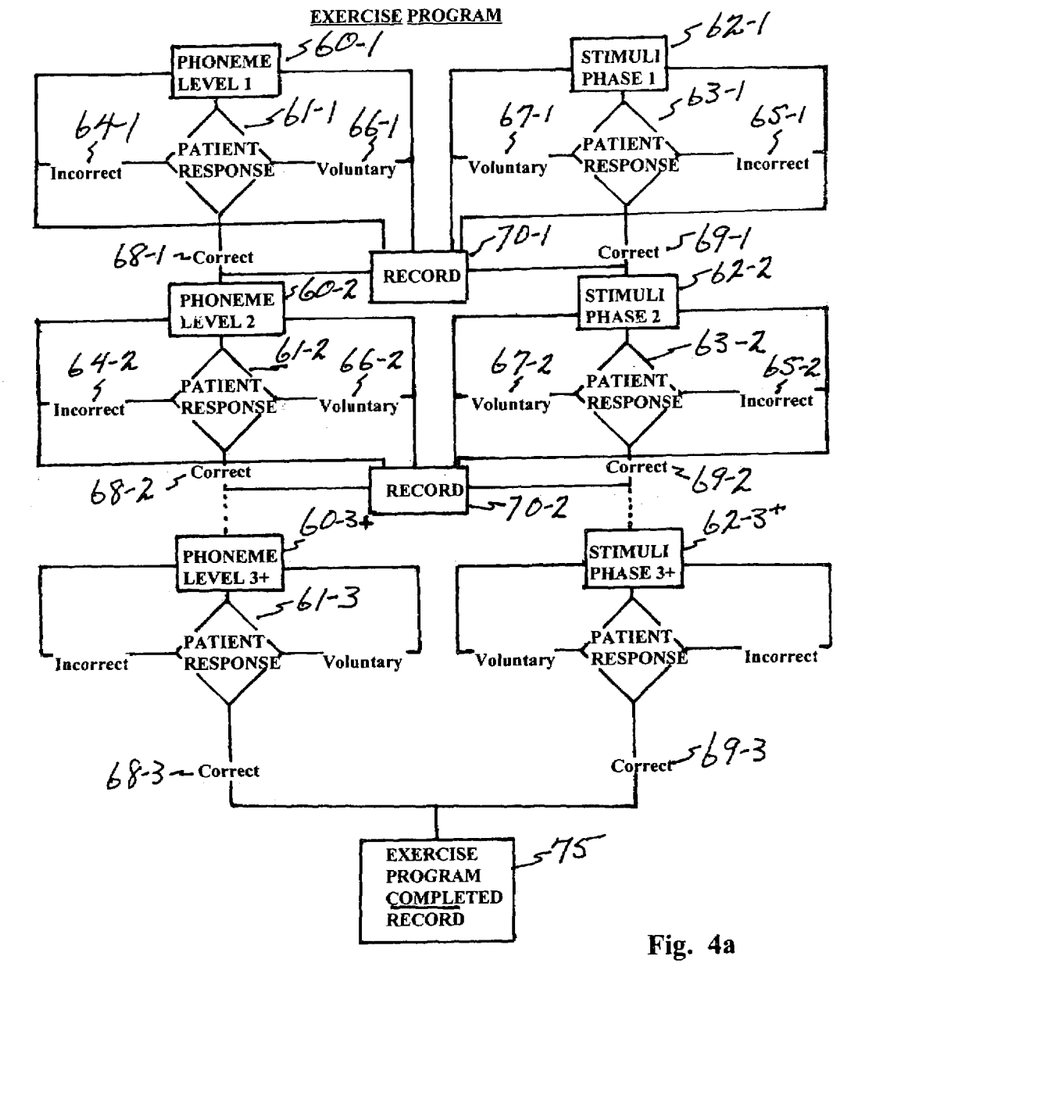
FIG. 4a is a flow chart representing, in more detail, the Exercise phase represented in FIG. 4.

Block 44, EXERCISE PROGRAM is represented in an expanded form in the flow chart in FIG. 4*a*. The Exercise Program is a series of therapeutic exercises for overcoming the problem of stuttering. During the Exercise Program, the breathing or respiratory pattern of the patient is monitored and administrated, block 46, RESPIRATORY PATTERN MONITORING. If PATIENT RESPONSE, block 48, to the Exercise Program is Incorrect, 49, team corrective feedback is provided, block 50, CORRECTIVE FEEDBACK PRESENTATION. This may include a repeat, in whole or in part of the last completed exercise session, by the patient, as represented by 50'.

When the patient's response to the Exercise Program is satisfactory or Correct, 51, or the Exercise Program is completed, block 52 EXERCISE PROGRAM COMPLETE, and the patient moves on, therapy-wise, to the self-administered, portion of the stuttering treatment program. This is a portion of the stuttering treatment program that may be referred to as a Preventive Maintenance portion of the program. The self-administrated portion of the stuttering treatment program is a self-disciplined, self-treatment and self-monitored portion of the stuttering treatment program.

In order to enter the Post Treatment phase of the stuttering treatment program self-administered exercises are selected, block 53, CHILD SELECTED EXERCISE. If the patient has adult status, the exercises are elected, block 54, ADULT ELECTED EXERCISE. The patient has overcome those physical and/or mental problems, with attendant emotional problems, that have caused the patient to stutter. These are usually persistent problems that, if ignored, will reoccur. Preventive maintenance is a positive part of the stuttering treatment program designed to prevent reoccurrence of the problems that originally caused the patient to stutter.

For a patient who is a child and/or is considered incapable of making his or her own decision, with respect to the stuttering treatment exercises, self-disciplined exercise is suggested and/or selected by the attending team, block 52. The selected exercise or exercises, at this stage of the stuttering treatment program, will be self-administrated, self-monitored and self-evaluated, for personal maintenance of speech fluency. This is represented by POST TREATMENT/MAINTENANCE/MONITORING. The term, MAINTENANCE, block 56, is defined as "preventive maintenance". Block 56 is more fully defined in the flow chart in FIG. 4*b*.

If the patient is an adult, he or she may elect the self-disciplined exercise or exercises, block 54, ADULT ELECTIVE EXERCISE. The present stuttering treatment program positively includes a post treatment period of maintenance or preventive maintenance, to prevent return of the stuttering problem. While full participation in the stuttering program's post treatment is highly recommended, full participation in the post treatment program is Optional, 55, to adult patients.

Attention is directed to FIG. 4*a*, which is a flow chart defining, more fully, the Exercise Program, block 44 in FIG. 4. The active exercise program is a series of exercises relating to stimuli and phoneme with monitoring and administration of respiratory action of the patient during the exercises. The initial stimuli and phoneme exercises are at the lowest complexity or stage and each increases in complexity until mastered or handled correctly. Block 60-1, PHONEME LEVEL 1 represents the least complex level of phoneme exercise, for that particular patient. Block 62-1, STIMULI COMPONENT 1 represents the least complex component of stimuli for that particular patient. If the patient's response, blocks 61-1 and 63-1 is Correct 68-1 and 69-1 the patient advances to the next complexity of exercises, blocks 60-2 and 61-2. If Patient Response, blocks 61-1 and/or 62-1 is Incorrect 64-1 and/or 65-1, the particular exercise to which the response was Incorrect will be repeated by the patient. If the patient is not satisfied with his or her response, Voluntary 66-1 and/or 67-1, repetition of the exercise or exercises are provided for. A full Record, block 70-1 (and 70-2) is maintained at each stage of exercise.

The next exercise stage is PHONEME LEVEL 2, block 60-2 and STIMULI COMPONENT, block 62-2 with Patient Response 61-2 and 63-2. As in the first stage of the exercises, Incorrect 64-2 and/or 65-2 Patient Response provides a repeat of the last performed exercise. A Voluntary 66-2 and/or 67-2 repeat of exercise is also provided.

Block 60-3+ and 62-3+ each represent the next and/or subsequent exercise stages in the program, each with increasing complexity and each with the same repetitive capability. When the last in the series of exercises has a Correct 68-3 and 69-3, Patient Response 61-3 and 63-3, the hands-on Exercise Program is completed, block 75.

Figure 4B:
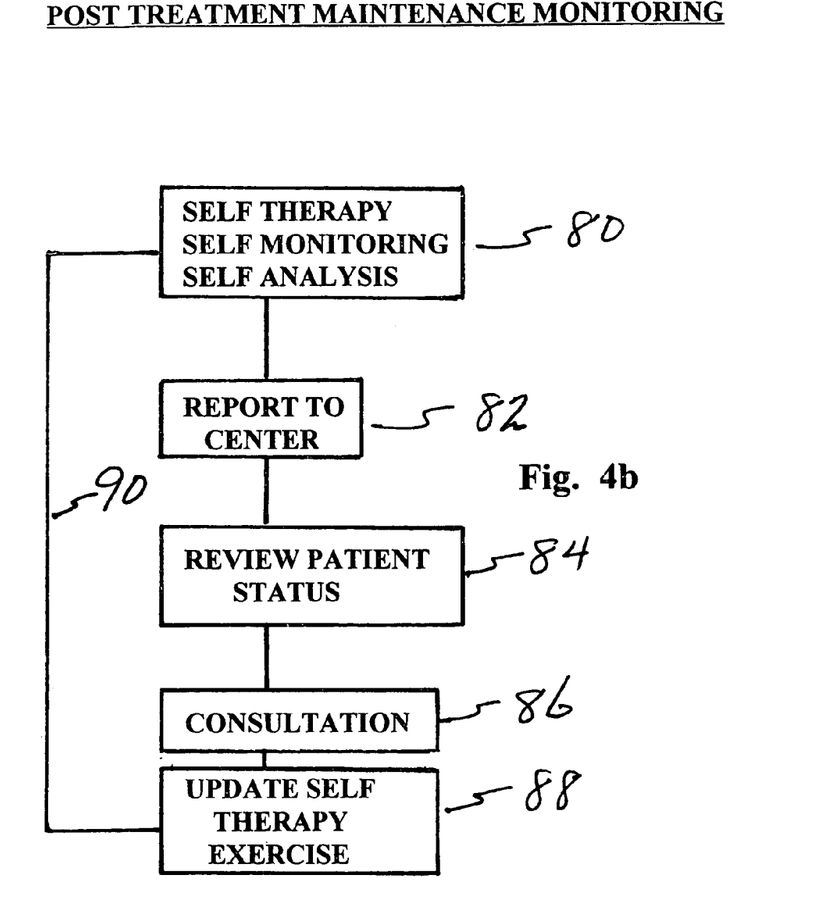
FIG. 4b is a flow chart representing, in more detail, the Post Treatment/Maintenance/Monitoring phase represented in FIG. 4; and, FIG. 5 is a flow chart representing interaction between a patient and center in the self-treatment phase of the program.

Attention is directed to FIG. 4*b*, which is a flow chart which represents or defines more fully, block 56 in FIG. 4. Block 80, SELF THERAPY/SELF MONITORING/SELF ANALYSIS effectively defines the therapeutic environment of the patient. The exercises selected or elected, as represented by blocks 53 and 54 of FIG. 4, are self-administered during this phase of the stuttering treatment program for maintaining the speech fluency developed during the hands-on phase of the stuttering treatment program. Self-monitoring and self-analysis of the effectiveness of the self-administered exercises serves as preventive maintenance and prevents regression of the patient to former poor speech habits. Through self-analysis the status of speech fluency is recognized. Block 82, REPORT TO CENTER, represents patient responsibility for communicating the status data of the patient to the Center. The exercise performed by the patient under the patient's supervision is known and with the status data from the patient full review, block 84 of the patient may be accomplished. Consultation, block 86, with the patient provides guidance and/or up-dates the self therapy, block 88. The self-administered therapy with self-monitoring and self-evaluation is repeated, as represented by the return line 90.

Figure 5:
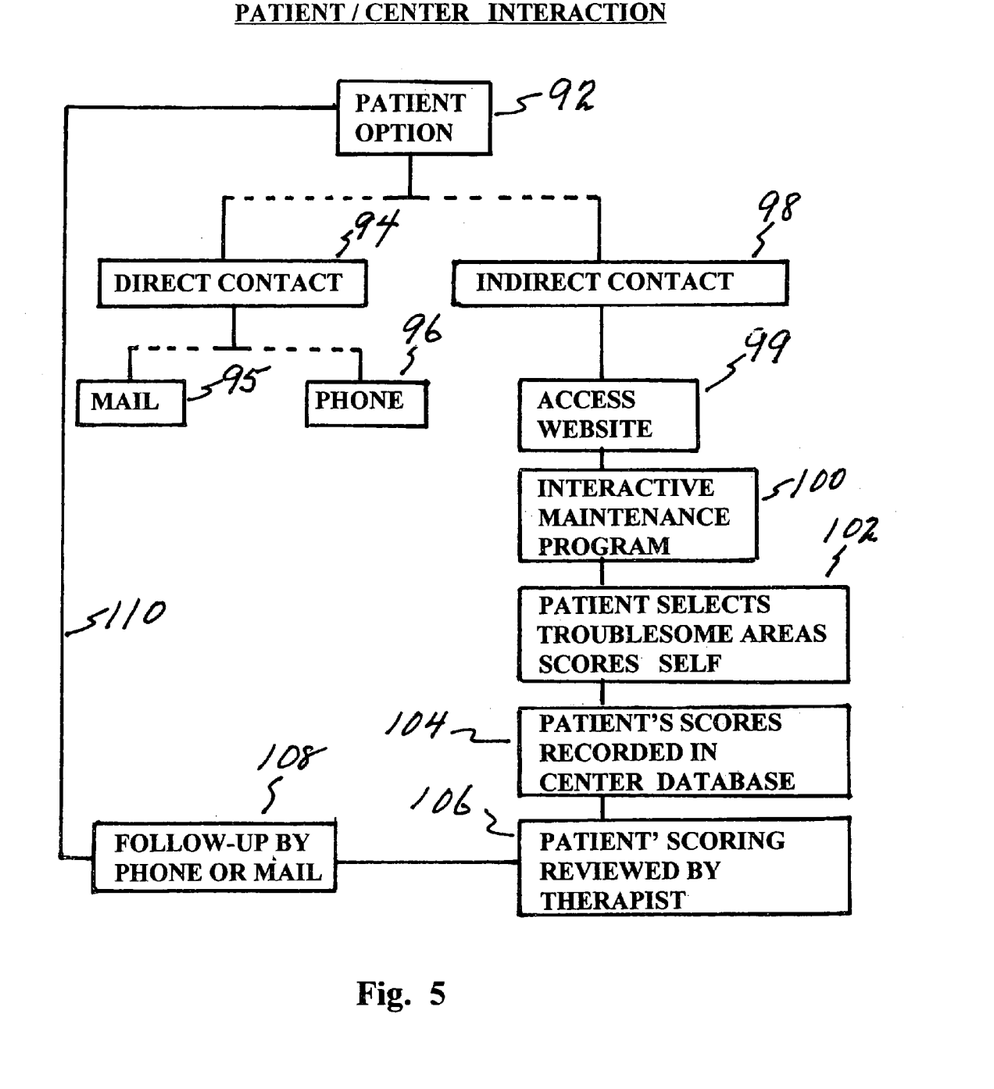

FIG. 5 represents and/or defines the interaction provisions between the patient and the Center, during the self-administered therapy phase of the stuttering treatment program. At the patient's option, block 92, contact with the Center may be made direct, block 94, or indirect, block 98. Direct contact may be via MAIL, block 95 or by PHONE, block 96. Indirect contact is provided over the Internet. The stuttering treatment program provides for a website on the Internet for those patients who use the Internet. The patient accesses the website, block 99, at which is provided an INTERACTIVE MAINTENANCE PROGRAM, block 100. The Interactive Maintenance Program includes a broad form questionnaire with questions covering potential problematic areas. The patient uses the questionnaire for identifying troublesome areas and scores himself or herself, block 102. The data is recorded in the Center database, block 104 and is reviewed by a therapist, block 106. Follow-up contact by personnel at the Center may be by phone or mail, block 108, U.S. Mail or E-Mail for example. As represented by the return line 110, the patient continues the post treatment portion of the stuttering treatment program.

In the foregoing description of the invention, referenced to the drawings, certain terms have been used for conciseness, clarity and comprehension. However, no unnecessary limitations are to be implied from or because of the terms used, beyond the requirements of the prior art, because such terms are used for descriptive purposes and are intended to be broadly construed. Furthermore, the description and illustration of the invention are by way of example, and the scope of the invention is not limited to the exact details shown, represented or described.

Having now described a preferred embodiment of the invention, in terms of features, discoveries and principles, along with certain alternative construction and suggested changes, other changes that may become apparent to those skilled in the art may be made, without departing from the scope of the invention defined in the appended claims.

What is claimed is:

1. A method for treating a stutterer for attaining fluent speech by said stutterer, comprising the steps of:
   a) performing a multi-dimensional diagnostic procedure on said stutterer including;
      i) a psychological evaluation,
      ii) a vocal parameters evaluation,
      iii) a respiratory pattern evaluation,
      iiii) a facial muscle activity analysis,
      v) measuring articulatory mobility, and
      vi) a laryngeal function analysis,
   for obtaining data on said stutterer for formulating a therapeutic program for attaining fluent speech for said stutterer;
   b) performing a series of supervised phoneme exercises and a series of stimuli exercises, each supervised exercise in each series being progressively increased in complexity, while simultaneously monitoring and adjusting a respiratory pattern of said stutterer, for attaining fluent speech; and
   c) performing a stutter patient-administered speech fluency exercise, defining a speech fluency preventive maintenance program for avoiding speech fluency regression of said stutter patient.

2. A method as in claim 1 and further including the step of:
   d) self-analyzing the effectiveness of said stutter patient-administered speech fluency exercises.

3. A method as in claim 2 and further including the step of:
   e) reconsidering said stutter patient-administered speech fluency exercises for said stutter patient.

4. A method as in claim 3 and further including the step of:
   f) up-dating said stutter patient-administered speech fluency exercise.

5. A method for overcoming a speech stuttering problem in a patient comprising the steps of:
   a) performing a multi-dimensional diagnostic procedure on a patient including
      i) performing a psychological evaluation,
      ii) performing a vocal parameters evaluation,
      iii) performing a respiratory pattern evaluation,
      iiii) analyzing facial muscle activity,
      v) measuring articulatory mobility, and
      vi) analyzing laryngeal function
   for obtaining data on said patient for formulating a therapeutic program for overcoming said speech stuttering problem of said patient for attaining speech fluency of said patient;
   b) modifying an attitude of said patient by adjusting psychological and physiological characteristics of said patient;
   c) providing a series of attended phoneme and stimuli exercises for said patient, said exercises defined by said therapeutic program, and said series of attended exercises being progressively increased in speech complexity;
   d) monitoring and adjusting a respiratory pattern of said patient concurrently with performance of step c); and
   e) performing a self-supervised speech fluency maintaining exercise for maintaining speech fluency of said patient.

6. A method as in claim 5 and further including the step of;
   f) self-monitoring said self-supervised speech fluency maintaining exercise for defining an effectiveness of said self-supervised speech fluency maintaining exercise on said patient.

7. A method as in claim 6 and further including the step of;
   g) self-analyzing speech fluency of said patient for evaluating the level of speech fluency retained after performance of self-supervised speech fluency maintaining exercise for providing a preventive maintenance of speech fluency.

8. A method as in claim 6 and further including the steps of;
   g) self-analyzing speech fluency of said patient for self-evaluating the level of speech fluency retained for determining speech fluency regression; and
   h) consulting with persons who formulated said therapeutic program for analyzing said level of speech fluency evaluated by said patient for receiving up-dated said self-supervised speech fluency maintaining exercise for preventive maintenance of speech fluency regression.

9. A method as in claim 6 and further including the step of;
   g) reporting a self-analysis of speech fluency retention to the professional persons who formulated said therapeutic program.

10. A method as in claim 9 and further including the step of;
   h) revising said self-supervised speech fluency maintaining exercise for preventing regression of speech fluency.

11. A method as in claim 9 and further including the step of;
   h) up-dating said self-supervised speech fluency maintaining exercise for preventing regression of speech fluency of said patient and communicating said up-dating to said patient.

12. A method as in claim 5 and further including the step of;
   f) self-monitoring said self-supervised speech fluency maintaining exercise and self-analyzing retained speech fluency for determining the effectiveness of said self-supervised speech fluency maintaining exercise on speech fluency of said patient.

13. An improved stuttering treatment method for attaining fluent speech for a person afflicted with stuttering where said stuttering treatment method provides for evaluating a plurality of characteristics of said person who stutters, for providing a supervised, hands-on program of breathing, phoneme and stimuli exercises of progressively increasing complexity for attaining fluent speech, the improvement including the steps of:
   a) providing a self-administered fluent speech maintaining exercise program for maintaining speech fluency attained during said supervised, hands-on program; and
   b) providing for self-evaluation of speech fluency retained during said self-administered fluent speech maintaining exercise for determining effectiveness of said self-administered fluent speech maintaining exercise against regression of speech fluency.

14. An improved stuttering treatment method as in claim 13 and further including the steps of:
   c) analyzing said self-evaluation for determining speech fluency level; and
   d) up-dating said self-administered speech exercise for maintaining speech fluency against regression.

15. An improved stuttering treatment method as in claim 14 and further including the step of:
   e) communicating said up-dated self-administered speech exercise to said person for self-supervised exercise.

16. A therapeutic program for overcoming the speech disorder of stuttering, comprising the steps of:
   a) performing a multi-dimensional procedure including,
     i) evaluating a stutterer psychologically,
     ii) evaluating vocal parameters of said stutterer,
     iii) evaluating a respiratory pattern of said stutterer,
     iiii) analyzing facial muscle activity of said stutterer,
     v) measuring articulatory mobility of said stutterer, and
     vi) analyzing a laryngeal function of said stutterer
   for obtaining data on said stutterer for formulating a therapeutic exercise program for said stutterer for attaining fluent speech for said stutterer;
   b) modifying an attitude of said stutterer, said attitude having been disoriented because of stuttering;
   c) performing, under hands-on supervision, speech exercises defined in said therapeutic exercise program including stimuli exercises and phoneme exercises while simultaneously monitoring and adjusting a respiratory pattern of said stutterer until speech fluency is attained; and
   d) performing self-supervised and self-administered preventive maintenance speech exercises for maintaining speech fluency of said stutterer.

* * * * *